United States Patent [19]
Numata et al.

[11] Patent Number: 5,859,203
[45] Date of Patent: Jan. 12, 1999

[54] MONOCLONAL ANTIBODIES FOR N-PEPTIDE

[75] Inventors: Yoshito Numata, Yao; Hidehisa Asada, Ibaraki; Keiji Dohi; Takahiro Fukunaga, both of Osaka; Yasushi Taniguchi, Takatsuki, all of Japan

[73] Assignee: Shionogi & Co., Ltd., Osaka, Japan

[21] Appl. No.: 907,747

[22] Filed: Aug. 8, 1997

Related U.S. Application Data

[62] Division of Ser. No. 569,461, Dec. 8, 1995, Pat. No. 5,702,910.

[30] Foreign Application Priority Data

Dec. 9, 1994 [JP] Japan .................................. 6-306453

[51] Int. Cl.$^6$ .................................................. G01N 33/53
[52] U.S. Cl. .......................... 530/380; 436/547; 436/548; 436/808; 530/380; 530/388.1; 530/388.15; 530/387.9; 530/808; 530/809; 530/829
[58] Field of Search ..................... 436/548, 547, 436/808; 530/388.1, 388.15, 380, 387.9, 808, 809, 829

[56] References Cited

FOREIGN PATENT DOCUMENTS

| 0 331 439 A2 | 9/1989 | European Pat. Off. ........ C12N 15/00 |
| 0 350 215 A2 | 1/1990 | European Pat. Off. ........ C12P 21/00 |
| 2-16997 | 9/1989 | Japan . |

OTHER PUBLICATIONS

M.G. Buckley et al., "Immunoreactive N–Terminal Pro–Atrial Natriuretic Peptide in Human Plasma: Plasma Levels and Comparisons with α–Human Atrial Natriuretic Peptide in Normal Subjects, Patients with Essential Hypertension, Cardiac Transplant and Chronic Renal Failure," *Clinical Science*, 77, pp. 573–579 (1989).

M.G. Buckley et al., "Concentrations of N–Terminal ProANP in Human Plasma: Evidence for ProANP (1–98) As The Circulating Form," *Clinica Chimica Acta*, 191, pp. 1–14 (1990).

M.G. Buckley et al., "N–Terminal Pro Atrial Natriuretic Peptide in Human Plasma," *American J. Hypertension*, 3, pp. 933–935 (1990).

E. Ishikawa et al., *Enzyme Immunoassay*, 3rd Ed., pp. 75–126 (1987).

H. Itoh et al., "γ–Atrial Natriuretic Polypeptide (γANP)–Derived Peptides in Human Plasma: Cosecretion of N–Terminal γANP Fragment and αANP," *J. Clinical Endocrinology and Metabolism*, 67, pp. 429–437 (1988).

B.F. Lindberg et al., "Radio–immunoassay of Atrial Natriuretic Peptide (ANP) and Characterization of ANP Immunoreactivity in Human Plasma and Atrial Tissue," *Scand. J. Clin. Lab. Invest.*, 52, pp. 447–456 (1992).

M. Mukoyama et al., "Preparation of Monoclonal Antibodies Against Atrial Natriuretic Polypeptide Precursor and Application to Highly Sensitive Sandwich Enzyme Immunoassay," *J. Hypertension*, 6 (suppl 4), pp. S320–S322 (1988).

J.A. Sundsfjord et al., "Identification and Plasma Concentrations of the N–Terminal Fragment of Proatrial Natriuretic Factor in Man," *J. Clinical Endocrinology and Metabolism*, 66, pp. 605–610 (1988).

T. Tsuji et al., "Stability of Human Atrial Natriuretic Peptide in Blood Samples," *Clinica Chimica Acta*, 225, pp. 171–177 (1994).

*Primary Examiner*—Christopher L. Chin
*Assistant Examiner*—Bao-Thuy L. Nguyen
*Attorney, Agent, or Firm*—James F. Haley, Jr.; Fish & Neave

[57] ABSTRACT

The present invention relates to a sandwich immunoassay for rapidly and readily measuring N-peptide using two kinds of monoclonal antibodies recognizing different portions of the N-peptide. The method for measuring N-peptide or a precursor thereof includes the steps of: incubating a mixture containing a sample and a first monoclonal antibody recognizing a portion of N-peptide; adding a labelled second monoclonal antibody recognizing a portion of N-peptide to the mixture, followed by further incubation; and detecting the resulting antigen-antibody complex in the mixture. Alternatively, the method includes the steps of: incubating a mixture containing a sample, a first monoclonal antibody recognizing a portion of N-peptide, and a labelled second monoclonal antibody recognizing another portion of N-peptide; and detecting the resulting antigen-antibody complex.

3 Claims, 5 Drawing Sheets

MONOCLONAL ANTIBODIES FOR N-PEPTIDE

This is a division of application Ser. No. 08/569,461, filed Dec. 8, 1995 entitled METHOD OF SANDWICH IMMUNOASSAY FOR N-PEPTIDE, now U.S. Pat. No. 5,702,910.

BACKGROUND OF THE INVENTION

1. Field of the Invention

The present invention relates to a method for rapidly and easily measuring N-peptide clinically useful for the diagnosis of cardiac incompetence and chronic renal failure, a monoclonal antibody used in the method, and a hybridoma producing the monoclonal antibody.

2. Description of the Related Art

Human atrial natriuretic polypeptide (hANP) is biologically produced as a peptide including 126 amino acids which is referred to as hANP(126) ($\gamma$-hANP). This $\gamma$-hANP accumulates in intra-atrial granules, and is secreted in response to an atrium pressure stimulus. At this time, $\gamma$-hANP is cleaved into hANP(1–98) (N-peptide) and hANP(99–126) ($\alpha$-hANP) and simultaneously released into the blood.

The blood level of $\alpha$-hANP reflects the cardiac conditions as marker in cardiac incompetence and chronic renal failure, and immunoassay thereof has already been employed for diagnostic purposes. However, the immunoassay has some disadvantages. For example, a very long reaction time (3 days) is required for the assay, and an immunological activity of a-hANP markedly decreases during the process of collecting or storage of a sample due to instability of a-hANP in the blood (See, T. Tsuji et al., Clin. Chim. Acta, 225, 171–177 (1994)). In contrast, N-peptide is more stable and lower in clearance than $\alpha$-hANP, the concentration of which is high in the circulatory blood. Therefore, immunoassay of the N-peptide has been developed.

It has already been reported that the immunoassay of the N-peptide which is an N-terminal peptide of the above-mentioned $\gamma$-hANP is useful for the diagnosis of cardiac incompetence and chronic renal failure (See, J. A. Sundsfjoed et al., J. Clin. Endocrionol. Metab., 66, 605–610 (1988); H. Itoh et al., J. Clin. Endocrinol., 67(3), 429–437 (1988); M. G. Burckley et al., Clin. Sci. 77, 573–579 (1989); and M. G. Burckley et al., Clin. Chim. Acta, 191, 1–14 (1990)). All of immunoassays for the N-peptide previously reported depend on competitive radioimmunoassay (RIA) methods using one kind of antibody. As a result, the methods require a long period of time (3 to 4 days), a limited temperature condition (about 4° C.), and/or a complicated operation (i.e., Sep-pak C-18 extraction) in which the plasma has to be pretreated (See, J. A. Sundsfjoed et al., supra; and M. G. Burckley et al., (1990) supra). Furthermore, any of these immunoassays have problems such as low precision and poor reproducibility. Thus, the development of a method for rapidly and easily measuring N-peptide has been required.

SUMMARY OF THE INVENTION

The method for measuring N-peptide or a precursor thereof according to the present invention includes the steps of: incubating a mixture of a sample and a first monoclonal antibody recognizing the N-peptide; adding a labelled second monoclonal antibody recognizing the N-peptide to the mixture, followed by further incubation; and detecting the resulting antigen-antibody complex in the mixture.

Alternatively, the method for measuring N-peptide or a precursor thereof according to the present invention includes the steps of: incubating a mixture of a sample, a first monoclonal antibody recognizing the N-peptide, and a labelled second monoclonal antibody recognizing the N-peptide; and detecting the resulting antigen-antibody complex in the mixture.

In one embodiment of the present invention, the first or second monoclonal antibody recognizes a portion of the amino acid sequence from the 43 position to the 66 position of the N-peptide.

In another embodiment of the present invention, the first or second monoclonal antibody is 7B6.

In another embodiment of the present invention, one of the first and second monoclonal antibodies is 7B6, and the other is a monoclonal antibody recognizing a portion of the amino acid sequence of the N-peptide, of which the recognition site is different from that of the 7B6.

In another embodiment of the present invention, one of the first and second monoclonal antibodies recognizes a portion of the amino acid sequence from the 43 position to the 66 position of the N-peptide, and the other recognizes a portion of the amino acid sequence from the 1 position to the 25 position of the N-peptide.

In another embodiment of the present invention, the other monoclonal antibody is KY-ANP-III.

In another embodiment of the present invention, the first monoclonal antibody recognizes a portion of the amino acid sequence from the 1 position to the 25 position of the N-peptide, and the second monoclonal antibody recognizes a portion of the amino acid sequence from the 43 position to the 66 position of the N-peptide.

In another embodiment of the present invention, the first monoclonal antibody is KY-ANP-III, and the second is 7B6.

In another embodiment of the present invention, the second monoclonal antibody is labelled with a radioisotope, an enzyme, a colloidal gold, a fluorescent substance, or a luminescent substance.

In another embodiment of the present invention, the second monoclonal antibody is labelled with a radioisotope or an enzyme.

According to another aspect of the present invention, the monoclonal antibody recognizing a portion of the amino acid sequence from the 43 position to the 66 position of the N-peptide is provided.

In one embodiment of the present invention, the monoclonal antibody is 7B6.

According to another aspect of the present invention, a hybridoma producing the above-mentioned monoclonal antibody is provided.

In one embodiment of the present invention, the hybridoma is mouse hybridoma 7B6 (FERM BP-4878).

According to another aspect of the present invention, an immunoassay kit of N-peptide or a precursor thereof including the above-mentioned monoclonal antibodies is provided.

Thus, the invention described herein makes possible the advantages of (1) providing a sandwich immunoassay method for N-peptide and a precursor thereof, the method being very useful for the diagnosis of cardiac incompetence, renal failure, and other circulatory diseases; (2) providing a monoclonal antibody used in the method; (3) providing a hybridoma producing the monoclonal antibody; and (4) providing an immunoassay kit for N-peptide or a precursor thereof containing the monoclonal antibody.

These and other advantages of the present invention will become apparent to those skilled in the art upon reading and understanding the following detailed description with reference to the accompanying figures.

DESCRIPTION OF THE PREFERRED EMBODIMENTS

Figure 1A:
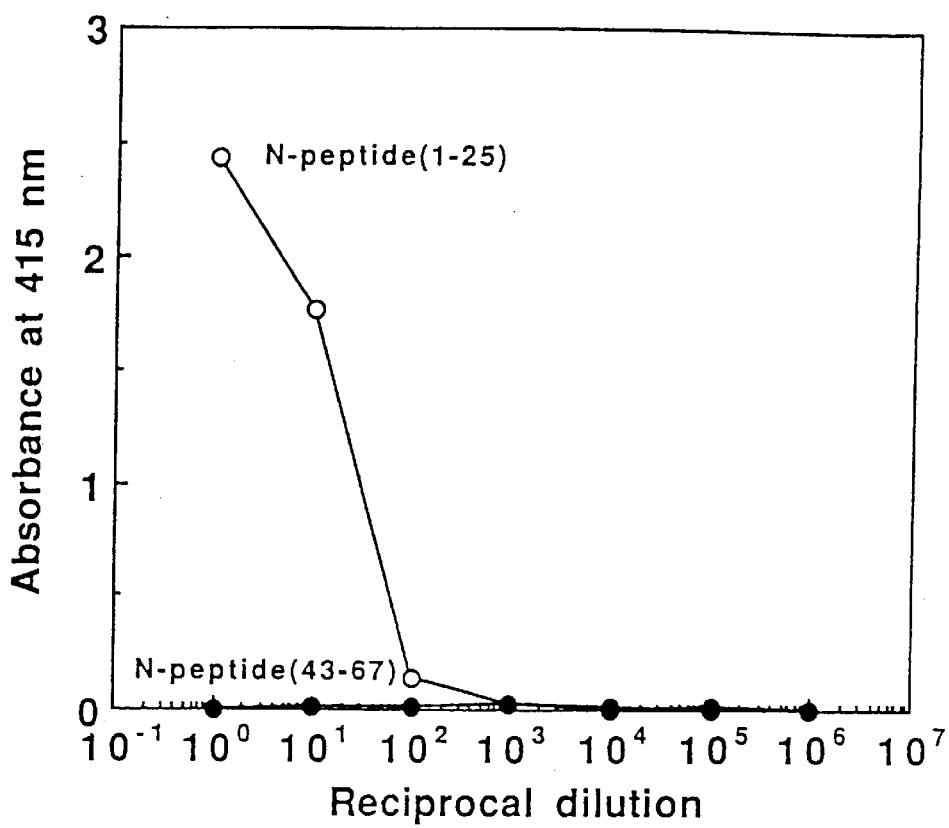
FIG. 1A shows reactivity of known monoclonal antibody KY-ANP-III with N-peptide(1–25) and N-peptide(43–67).

The inventors of the present invention conducted numerous studies for the purpose of rapidly, readily, and precisely measuring N-peptide and a precursor thereof. As a result, they produced a monoclonal antibody recognizing N-peptide and constructed sandwich immunoassays using the combination of two monoclonal antibodies, each recognizing different epitopes of the N-peptide, thereby achieving the present invention.

As used herein, the term "N-peptide" refers to a peptide including the amino acid sequence from the 1 position to the 98 position on an N-terminal region of γ-hANP. γ-hANP is cleaved into N-peptide and α-hANP when secreted in vivo, and α-hANP includes the amino acid sequence from the 99 position to the 126 position of γ-hANP. The term "N-peptide precursor" in the present specification includes γ-hANP.

As used herein, the term "N-peptide(X–Y)" refers to an amino acid sequence from the X position to the Y position of N-peptide. For example, the term "N-peptide (1–25)" refers to the amino acid sequence from the 1 position to the 25 position of N-peptide. The term "N-peptide(43–66)" refers to the amino acid sequence from the 43 position to the 66 position of N-peptide, and the term "N-peptide(43–67)" refers to the amino acid sequence from the 43 position to the 67 position of N-peptide. The term "N-peptide(43–66)Cys" refers to the amino acid sequence having an additional cysteine residue at the carboxyl terminus of N-peptide (43–66).

As used herein, the terms "N-peptide" and "N-peptide precursor" refer to a naturally occurring or chemically synthesized N-peptide and N-peptide precursor, respectively.

As used herein, the term "antibody" refer to an antibody and fragments thereof, including fragments such as Fab, Fab', and F(ab)$_2$ of the antibody.

As used herein, the term "KY-ANP-III antibody" which has been produced by Nakao et al. (Japanese Laid-Open Patent Publication No. 2-16997) refers to a monoclonal antibody recognizing a portion of N-peptide(1–25) which is the amino acid sequence from the 1 position to the 25 position of γ-hANP. The hybridoma producing the monoclonal antibody has been deposited with Fermentation Research Institute, Agency of Industrial Science and Technology of 1-3, Higashi 1-chome, Tsukuba-shi, Ibaraki which is a public depository, under the Budapest Treaty. The deposit was made on May 18, 1988 and accorded Accession No. FERM BP-1887.

The deposit was viable at the time of deposit and will be replaced by Applicants should they become non-viable.

The deposit will be made available to the Commissioner during pendency of the application under the terms of 37 CFR 1.14 and 35 USC 122, and will be maintained in the Fermentation Research Institute depository for a period of 30 years or 5 years after the last request, whichever is longer. At the time of grant of a patent based upon the present specification all restrictions upon availability to the public will be irrevocably removed.

Next, a method of the present invention will be described in the order of the steps. The production of the monoclonal antibody recognizing N-peptide and sandwich immunoassay using the monoclonal antibody can be conducted by a general process by those skilled in the art, unless otherwise specified.

(1) Immunization

In order to produce a monoclonal antibody recognizing N-peptide, an animal is immunized with an appropriate antigen. As the animal, a mouse, rat, or the like can be used. As the antigen, an amino acid fragment which is a portion of N-peptide can be used. This antigen is made an immunogen suitable for immunization. In order to use this antigen as an immunogen, for example, N-peptide(43–66)Cys can be conjugated with a carrier protein. As the carrier protein, high molecular weight materials such as bovine serum albumin (BSA), hemocyanin, and bovine thioglobulin (BTG) can be used. A maleimide compound or the like can be used for conjugation. The maleimide compound is a bifunctional crosslinker, including succinimidyl 4-(N-maleimidomethyl) cyclohexane-1-carboxylate (SMCC), m-maleimidobenzoyl-N-hydroxysuccinimide ester (MBS), succinimidyl 4-(p-maleimidophenyl)butyrate (SMPB), as well as sulfo-MBS, sulfo-SMCC, and the like. A succinimidyl group of these crosslinkers reacts with a primary amine and further reacts with the thiol-reactive maleimide to form a covalent bond with the thiol of a cysteine residue. The immunogen thus obtained is emulsified in an appropriate adjuvant such as Freund's complete adjuvant and immunization is conducted by intraperitoneally applying the resulting emulsion to an animal. Preferably, the animal is intraperitoneally, subcutaneously, or intravenously boosted with the immunogen several times at intervals of several weeks.

(2) Production of a monoclonal antibody

A hybridoma producing a monoclonal antibody recognizing N-peptide can be produced by fusing a spleen cell with a myeloma cell. The spleen cell is derived from the animal, preferably a mouse, immunized in the above item (1). The myeloma cell is derived from mammals, preferably a murine myeloma cell. Polyethylene glycol or the like can be used for cell fusion. A desired hybridoma can be selected by screening and cloning a hybridoma obtained by fusion.

In order to produce a monoclonal antibody, the hybridoma is cultured in vitro or in vivo. Preferably, the hybridoma is cultured in vivo. For example, the hybridoma is intraperitoneally administered to a mouse in order to produce ascites containing a monoclonal antibody. The monoclonal antibody can easily be obtained and purified from the ascites by any method known to those ordinarily skilled in the art.

The monoclonal antibody of the present invention can be applied to the sandwich immunoassay of the present invention as well as other immunoassays such as a competitive immunoassay and another type of immunoassay with two antibodies.

(3) Immunoassay

The immunoassay of the present invention is based on a sandwich immunoassay including the steps of: fixing an antibody (first monoclonal antibody) on a solid phase and incubating the fixed first monoclonal antibody with a sample containing an antigen; adding a labelled second monoclonal antibody which is different from the first antibody and incubating the resulting mixture; and detecting the produced labelled antigen-antibody complex in the mixture. In the immunoassay of the present invention, a sample, the first monoclonal antibody and the labelled second monoclonal antibody may be incubated simultaneously.

In terms of a detection method, the sandwich immunoassay of the present invention includes a sandwich radioimmunoassay (RIA), a sandwich enzymeimmunoassay (EIA), a sandwich fluoroimmunoassay (FIA), a sandwich chemiluminescence immunoassay (CLIA), a sandwich chemiluminescence-enzymeimmunoassay (CLEIA) and an immunochromatographic method based on the sandwich assay. Preferably, the RIA and the EIA can be used.

The first monoclonal antibody of the present invention can be immobilized on a solid phase such as a microtiter plate, bead, tube, membrane, filter paper, or plastic cup. In particular, a polystyrene bead is preferably used.

Samples to be measured can be those containing N-peptide and a precursor thereof, and include a plasma, a serum, blood, urine, and the like.

The second monoclonal antibody of the present invention can be labelled with a radioisotope, an enzyme, a fluorescent substance, or a luminescent substance. The labelling can be performed by any method known to those skilled in the art.

Examples of the radioisotope used for labelling include $^{14}C$, $^{3}H$, $^{32}P$, 125I, and 131I. In particular, 125I can be used in a preferred embodiment. These radioisotopes can be bound to the monoclonal antibody by the chloramine T method, the peroxidase method, the Iodogen method, or Bolton-Hunter method.

Examples of the enzyme which can be used for labelling include β-galactosidase (βGAL), alkaline phosphatase (ALP), and horseradish peroxidase (HRP). These enzymes can be bound to the monoclonal antibody by the Nakane method, or a method of Ishikawa et al. (pp. 75– 127, in "Enzyme immunoassay," by E. Ishikawa, et al., 3rd ed., 1987, Igakushoin).

Examples of the fluorescent substance which can be used for labelling include fluorescein, fluorescamine, fluorescein isothiocyanate, and tetramethyl rhodamine isothiocyanate.

Examples of the luminescent substance which can be used for labelling include luciferin, a luminol derivative, and an acridinium ester.

Colloidal gold can be used for labelling.

In a preferred embodiment, an N-peptide sandwich RIA can be performed. Specifically, the N-peptide sandwich RIA is performed as follows: A bead on which the first monoclonal antibody has been immobilized is added to a standard N-peptide solution or sample, and the resulting mixture is incubated at a temperature of 4° C. to 45° C., preferably at 25° C. to 37° C., for 1–4 hours, preferably for 2 hours. Thus, a first reaction is conducted. The bead is washed, and then a solution containing the second monoclonal antibody labelled with a radioisotope such as $^{125}I$ is added to the bead. The resulting mixture is incubated at a temperature of 4° C. to 45° C., preferably at 25° C. to 37° C., for 1–4 hours, preferably for 2 hours. Thus, a second reaction is conducted. The bead is washed, and then the radioactivity of the antigen-antibody complex bound on the bead is detected by a γ-ray counter to determine the amount of N-peptide.

It is considered that N-peptide is more stable compared with α-hANP and a decrease in immunological activity during a sample collecting operation is small, so that N-peptide can also be applied to the following non-RIA.

In another preferred embodiment, the N-peptide sandwich EIA can be performed. Specifically, the N-peptide sandwich EIA is performed as follows: A bead on which the first monoclonal antibody has been immobilized is added to a standard N-peptide solution or sample, and the resulting mixture is incubated at a temperature of 4° C. to 45° C., preferably at 25° C. to 37° C., for 2 hours. Thus, the first reaction is conducted. The bead is washed, and then a solution containing the second monoclonal antibody labelled with an enzyme such as HRP is added to the bead. The resulting mixture is incubated at a temperature of 4° C. to 45° C., preferably at 25° C. to 37° C., for 2 hours. Thus, the second reaction is conducted to form an antibody/N-peptide/antibody complex on the bead. The enzyme activity retained on the bead is colorimetrically determined through a specific substrate, from which the amount of N-peptide trapped on the bead can be determined. The calorimetric determination may be made with a conventional spectrophotometer or the like.

As described above, the immunoassay of the present invention is a sandwich immunoassay using two kinds of antibodies recognizing different epitopes. Therefore, compared with a conventional competitive method using one kind of antibody, the sandwich immunoassay of the present invention has high sensitivity, as well as outstanding precision, readiness, and rapidness.

EXAMPLES

The present invention will be described in detail by way of illustrative examples.

EXAMPLE 1

Production of a monoclonal antibody recognizing a portion of N-peptide(43–66)Cys and a hybridoma producing the antibody A. Preparation of an immunogen and immunization For the purpose of measuring N-peptide by sandwich immunoassay, a monoclonal antibody recognizing a portion of N-peptide, of which the recognition site is different from that of the known monoclonal antibody KY-ANP-III was produced as described below. N-peptide(43–66)Cys was used as an antigen.

First, 33.5 mg of bovine thioglobulin (BTG, available from Sigma) as a carrier protein was dissolved in 5 ml of 0.1M phosphate buffer (pH 7.0)(Buffer A). Then, 1.2 ml of Buffer A containing 10.5 mg of sulfosuccinimidyl 4-(N-maleimidomethyl)-cyclohexane-1-carboxylate (sulfo-SMCC, available from Pierce) was added. The resulting mixture was allowed to react at 30° C. for 1 hour, thereby a maleimide derivative of BTG was obtained. The reaction mixture was applied to a Sephadex G-25 column (Pharmacia) equilibrated with 0.1M phosphate buffer (pH 6.0)(Buffer B), and void fractions containing the maleimide-linked BTG were collected. Then, 0.4 ml of Buffer B containing 3.3 mg of N-peptide(43–66)Cys (Peptide Institute, Inc.) and 2.5 mM of EDTA was added to 2.6 ml of Buffer B containing 6 mg of the maleimide derivative of BTG, and the mixture was allowed to react at 4° C. for 20 hours. Thereafter, the reaction was stopped by adding 40 μl of 50 mM N-ethylmaleimide. The reaction mixture thus obtained was applied to a Sephadex G-50 column (Pharmacia) equilibrated with Buffer B, and void fractions were collected so as to remove a peptide remaining unchanged. The collected fractions were dialyzed against water at 4° C. overnight and lyophilized. As a result, 10.9 mg (dry weight) of N-peptide(43–66)Cys-BTG conjugate was obtained and used as an immunogen as follows.

Immunization was conducted by intraperitoneal administration of 100 μg of the conjugate per BALB/c mouse. Boost was performed 3 times at 3 or 4 weeks intervals. In the first and second immunizations, the conjugate was administered with Freund's complete adjuvant.

B. Production of a hybridoma producing 7B6 antibody and production of the 7B6 antibody using the hybridoma A spleen cell ($1.1 \times 10^8$) obtained from the mouse immunized in the above item A on the third day after the final immunization was fused with a mouse myeloma cell (P3-U1-X63-Ag8, Tokyo Shuryu Research Institute, $2.1 \times 10^7$) using 50% polyethylene glycol 4000 (Merck). The hybridoma thus obtained by fusion was obtained by the use of a selective medium containing hypoxanthine, aminopterin, and thymidine. On the 10th day after cell fusion, a hybridoma producing a specific antibody was screened. An EIA used for screening was performed as follows: 50 μl of PBS (phosphate buffer (pH 7.4) containing 0.15M NaCl) containing 1 μg of N-peptide(43–67) (Peptide Institute, Inc.) or N-peptide(1–25) (Peptide Institute, Inc.) was added to each well of 96-well microtiter plate (Nunc) and allowed to bind the peptides thereon by keeping each well at 4° C. overnight. The wells were then washed once with a solution containing 25% Block Ace (Dainippon Pharmaceutical Co., Ltd.), and 300 μl of this solution was added to the wells to conduct blocking. Then, the wells were washed three times with PBS containing 0.05% Tween 20, and 50 μl of culture supernatant of the hybridoma was added to the wells, and the mixture was allowed to react at room temperature for 2 hours. The wells were then washed three times, 50 μl of 25% Block Ace solution containing 5 μg of HRP-labelled anti-mouse IgG was added to the wells, and the mixture thus obtained was allowed to react at room temperature for 1 hour. The wells were washed three times, and 50 μl of solution containing 4 mM of 2,2'-azino-bis(3-ethylbenzothiazoline-6-sulfonic acid)(ABTS, Boehringer-Mannheim) and 2 mM of $H_2O_2$ was added to the wells, whereby the reaction of HRP in the wells was conducted at room temperature for 15 minutes. Then, the reaction was stopped by adding 50 μl of 0.002% $NaN_3$ solution. The absorbance of each well was measured at 415 nm by a plate reader (MTP-32, Corona).

Hybridomas in wells which showed positive production of monoclonal antibodies were cloned three times by a limiting dilution, whereby hybridomas producing monoclonal antibodies recognizing N-peptide(43–66) were obtained.

A sub-class of antibodies produced by the hybridomas was determined by using the culture supernatant of the hybridomas. A mouse monoclonal antibody isotyping kit (Amersham Corp.) was used for this determination. A monoclonal antibody newly obtained was designated as 7B6, belonging to the isotype $IgG_1(\kappa)$.

Figure 1B:
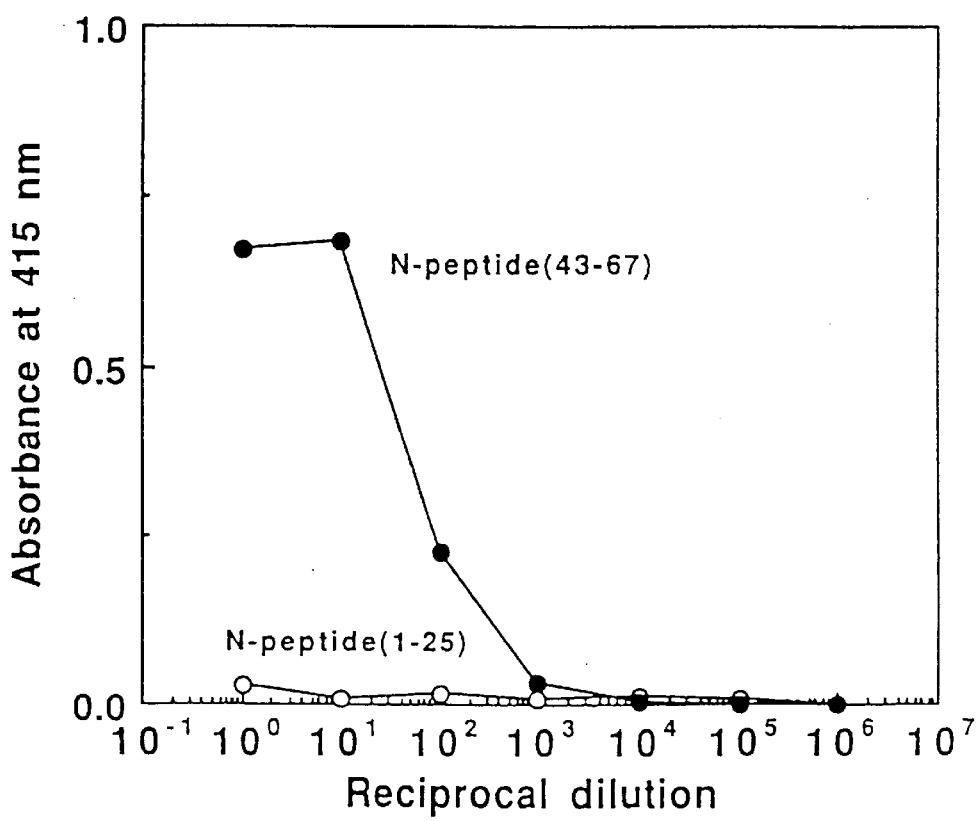
FIG. 1B shows reactivity of monoclonal antibody 7B6 of the present invention with N-peptide(1–25) and N-peptide (43–67).

The reactivities of the known monoclonal antibody KY-ANP-III ($IgG_1\kappa$) and the new monoclonal antibody 7B6 with various kinds of N-peptide fragments were confirmed by the above-mentioned EIA method. As the KY-ANP-III, a monoclonal antibody produced by a hybridoma FERM BP-1887 was used. The results are shown in FIG. 1. In this figure, ○ represents reactivity with N-peptide(1–25) and ● represents reactivity with N-peptide(43–67). The KY-ANP-III antibody reacted with N-peptide(1–25), but not with N-peptide(43–67) (FIG. 1A). In contrast, the 7B6 antibody reacted with N-peptide(43–67), but not with N-peptide (1–25) (FIG. 1B). Thus, it was confirmed that two antibodies recognize different portions of N-peptide, respectively, that is, the KY-ANP-III antibody recognizes the 1–25 amino acid sequence of N-peptide and the 7B6 antibody recognizes the 43–66 portion of N-peptide.

The hybridoma producing the monoclonal antibody 7B6 of the present invention was deposited with National Institute of Bioscience and Human-Technology, Agency of Industrial Science and Technology of 1-3, Higashi 1-chome, Tsukuba-shi, Ibaraki, which is a public depository, under the Budapest Treaty. The deposit was made on Nov. 9, 1994 and accorded Accession No. FERM BP-4878.

The deposit was viable at the time of deposit and will be replaced by Applicants should it become non-viable.

The deposit will be made available to the Commissioner during pendency of the application under the terms of 37 CFR 1.14 and 35 USC 122, and will be maintained in the National Institute of Bioscience and Human-Technology depository for a period of 30 years or 5 years after the last request, whichever is longer. At the time of grant of a patent based upon the present specification all restrictions upon availability to the public will be irrevocably removed.

EXAMPLE 2

Purification of monoclonal antibody 7B6 from ascites of a mouse

Two weeks after intraperitoneal administration of 0.5 ml of pristane to mice (BALB/c), approximately $1 \times 10^7$ hybridomas obtained in Example 1 were intraperitoneally administered to each of the mice. On the 7th to 10th day after administration, ascites was collected and centrifuged at 10,000×g for 20 minutes. Then, the supernatant was diluted by a factor of two with PBS and applied to a Protein G Sepharose column (Pharmacia). The column was washed with PBS. Then, the column was eluted with 0.2M glycine-HCl buffer (pH 2.7) and the eluate was immediately neutralized with 1M Tris buffer. The eluate was salted out with 50% saturated ammonium sulfate at 0° C. The precipitate was collected by centrifugation at 10,000×g for 20 minutes. The precipitate thus obtained was dissolved in PBS and dialyzed against PBS at 4° C. overnight to give purified 7B6 monoclonal antibodies.

EXAMPLE 3

Production of beads on which a KY-ANP-III antibody is immobilized

Polystyrene beads (Immunochemical) previously treated with 1% glutaraldehyde aqueous solution were immersed in 25 μg/ml of a KY-ANP-III antibody solution (one bead/200 μl) in 0.05M phosphate buffer (pH 7.1). KY-ANP-III antibody which is a monoclonal antibody recognizing N-peptide (1–25) was obtained by cultivating a hybridoma (FERM BP-1887) producing the antibody. The mixture of polystyrene beads and the KY-ANP-III antibody was shaken at 25° C. for 3 hours and further shaken at 4° C. for at least 19 hours. The aqueous portion was removed by aspiration, and the polystyrene beads were washed with 0.05M phosphate buffer (pH 7.1). Thereafter, 0.05M phosphate buffer (pH 7.1) containing 25% Block Ace was added to the beads for blocking at 4° C. for at least 40 hours, whereby the beads on which the KY-ANP-III antibody was immobilized were obtained. The beads thus obtained were preserved in 0.1M phosphate buffer (pH 6.5) containing 0.15M sodium chloride, 0.1% BSA, 1 mM of EDTA, and 0.1% sodium azide.

EXAMPLE 4

Labelling of 7B6 antibody with radioactive iodine ($^{125}I$)

A purified 7B6 antibody was labelled with $^{125}I$ by the chloramine T method as follows:

First, 100 μl of 0.5M phosphate buffer (pH 7.5) and 2 mCi/20 μl of Na$^{125}$I (Amersham Corp.) were placed in a glass tube. Then, 60 μl of 3.3 mg/ml 7B6 antibody solution in PBS and 20 μl of 1 mg/ml chloramine T solution in 0.5M phosphate buffer (pH 7.5) were added to the glass tube and stirred. The mixture was allowed to react at room temperature for 30 seconds, and the reaction was stopped by adding 20 μl of 2.5 mg/ml sodium pyrosulfite solution in 0.1M phosphate buffer (pH 7.5). Then, 20 μl of 50 mg/ml potassium iodide aqueous solution was added to the reaction mixture, and the mixture was applied on Superose 12 (1×30 cm) (Pharmacia) and eluted with 0.1M phosphate buffer (pH 7.0) to give $^{125}$I-labelled 7B6 antibody fractions.

EXAMPLE 5

Sandwich RIA

Standard solutions containing a series of concentrations of N-peptide(1–67)(Peptide Institute, Inc.) were prepared. Fifty μl of the standard solution or a sample was placed in each of a predetermined number of test tubes. Then, 250 μl of Buffer C which is a 0.1M phosphate buffer (pH 6.5) containing 0.15M sodium chloride, 0.1% BSA, 1 mM EDTA, and 0.1% Kathon CG (Rohm and Haas) was added to each test tubes. Each one of the beads coated by the KY-ANP-III antibody produced in Example 3 was added to the test tube. Each test tube was shaken at 200 strokes per minute at 25° C. for 2 hours (first reaction), the solution in each test tube was removed by aspiration, and the test tubes were washed three times with 2 ml of Buffer D (i.e., 0.05M phosphate buffer (pH 6.5) containing 1 mM EDTA, 0.0075% Tween 20, and 0.1% Kathon CG). Then, a second reaction was conducted as follows. Three hundred μl (about 200,000 cpm) of $^{125}$I-labelled 7B6 antibody solution diluted with Buffer D containing 0.1% BSA was added to each test tube, and the test tubes were shaken at 200 strokes per minute at 25° C. for 2 hours. The solution in the test tubes was removed by aspiration, and the test tubes were washed three times with 2 ml of Buffer D. The radioactivity retained on the bead in each test tube was measured by a γ-ray counter (ARC-600, Aroca).

Figure 2:
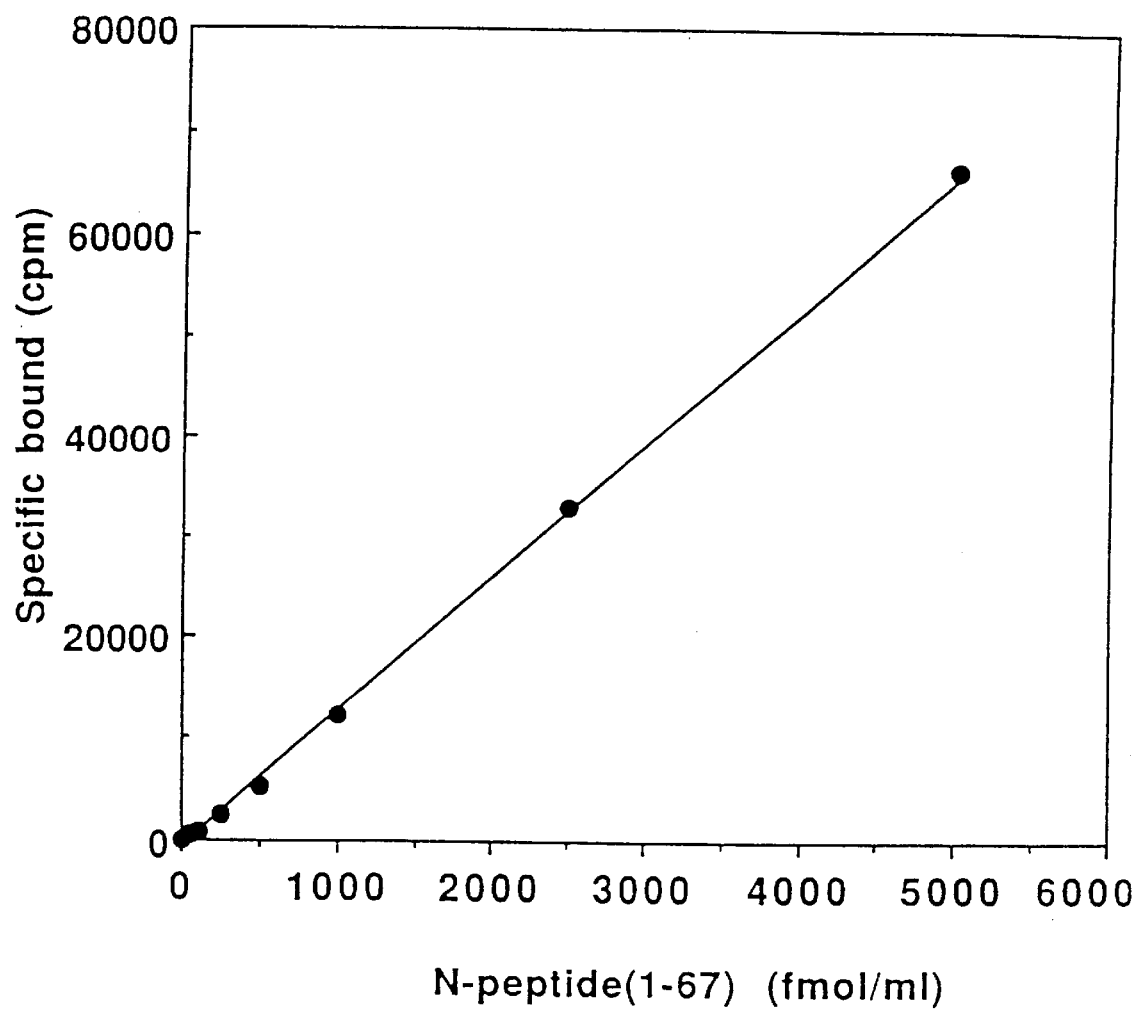
FIG. 2 shows a standard curve in the sandwich RIA of the present invention.

A standard curve obtained from the above-mentioned sandwich RIA is shown in FIG. 2. The radioactivity was proportional to the concentration of N-peptide(1–67) in the range of 0 to 5000 fmol/ml. The lowest sensitivity detectable was 40 fmol/ml. A reproducibility test was conducted on 4 samples of human plasma. The reproducibility test was conducted in order to confirm the precision of the method. There are two kinds of measurement methods: An intra-assay reproducibility test is made for confirming the variation of measured values on a single sample within one test. An inter-assay reproducibility test is made for confirming the variation of measured values between a number of tests carried out on a single sample. Tables 1 and 2 show the results of these two reproducibility tests. In the intra-assay reproducibility test, a coefficient of variation (CV) was 1.5% to 2.2% (Table 1), and in the inter-assay reproducibility test, CV was 4.1% to 5.6% (Table 2).

TABLE 1

Intra-assay reproducibility by Sandwich RIA

| Sample | n | Mean ± SD fmol/ml | CV % |
|---|---|---|---|
| Human plasma 1 | 10 | 283 ± 4.8 | 1.7 |
| Human plasma 2 | 10 | 836 ± 12.9 | 1.5 |
| Human plasma 3 | 10 | 2364 ± 52.5 | 2.2 |
| Human plasma 4 | 10 | 4232 ± 75.9 | 1.8 |

TABLE 2

Inter-assay reproducibility by Sandwich RIA [a]

| Sample | n | Mean ± SD fmol/ml | CV % |
|---|---|---|---|
| Human plasma 1 | 7 | 266 ± 14.9 | 5.6 |
| Human plasma 2 | 7 | 837 ± 42.4 | 5.1 |
| Human plasma 3 | 7 | 2217 ± 93.1 | 4.2 |
| Human plasma 4 | 7 | 3780 ± 156.0 | 4.1 |

[a] Seven separate assays were performed in triplicate over 7 days.

Figure 3:
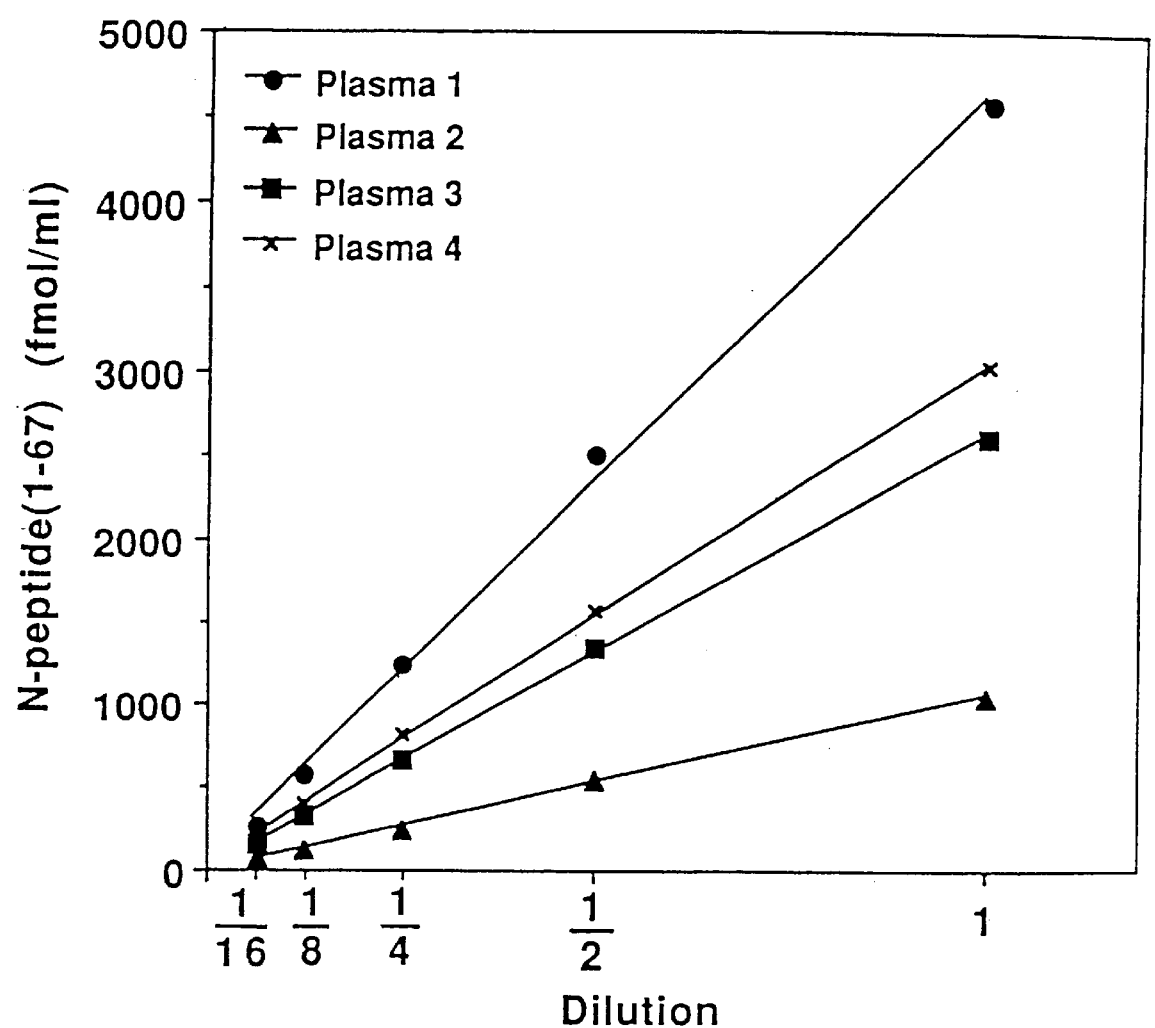
FIG. 3 shows a dilution curve tested in clinical samples by the sandwich RIA of the present invention.

Next, a dilution test was conducted on human plasma. Serial two-fold dilutions with Buffer C were performed on four samples of human plasma, resulting in a plurality of samples for measurement with various concentrations. The samples thus obtained were measured by the sandwich RIA method in the same way as above. The results are shown in FIG. 3. The data indicates that in any concentration each point is on a straight line which approximately intersects at the zero point.

Then, it was tested whether components considered to be present in the plasma had influence on the sandwich RIA. The results showed that the effects of binding-type bilirubin (0.15 mg/ml), free-type bilirubin (0.17 mg/ml), hemoglobin (4.25 mg/ml), and chyle (formazin turbidity, 24 degrees) were not found, and hence the components had no influence.

Thus, it was confirmed that N-peptide can be determined by the sandwich RIA of the present invention with good precision without being influenced by the other components in the plasma.

Furthermore, a recovery test in which a standard substance is added to a sample to be tested was conducted using human plasma. Four samples of human plasma were diluted by a factor of two with a standard N-peptide(1–67) solution containing N-peptide in a concentration of 250, 500, or 1000 fmol/ml. The samples thus obtained were measured by the sandwich RIA in the same way as described above. The results are shown in Table 3. The recovery of the N-peptide added was 88% to 134%. Thus, it was confirmed that various N-peptides in human plasma and the standard N-peptide show a quite similar reactivity in the sandwich RIA of the present invention.

TABLE 3

Recovery test for added substance by sandwich RIA

| Sample | Endogenous N-peptide (fmol/ml) | Added (fmol/ml) | Found [a] (fmol/ml) | Recovery (%) |
|---|---|---|---|---|
| Human plasma 1 | 2216 | 250 | 250 | 100 |
| | 2216 | 500 | 469 | 94 |
| | 2216 | 1000 | 1053 | 105 |
| Human plasma 2 | 2517 | 250 | 294 | 118 |
| | 2517 | 500 | 556 | 111 |
| | 2517 | 1000 | 1104 | 110 |
| Human plasma 3 | 1868 | 250 | 221 | 88 |
| | 1868 | 500 | 513 | 103 |
| | 1868 | 1000 | 998 | 100 |
| Human plasma 4 | 2282 | 250 | 336 | 134 |
| | 2282 | 500 | 515 | 103 |
| | 2282 | 1000 | 961 | 96 |

[a] Increase over endogenous N-peptide

Next, the concentration of N-peptide in plasmas of 36 healthy subjects (23 males and 13 females) was measured by the sandwich RIA of the present invention. As a result, the average value was 213 fmol/ml and the standard deviation was 90 fmol/ml.

EXAMPLE 6

Labelling of 7B6 antibody with horseradish peroxidase (HRP)

A purified 7B6 antibody was labelled with HRP by a method of Ishikawa et al., supra, as follows:

First, 4.5 ml of 0.2M citrate buffer (pH 4.0) and 0.9 ml of 2.2 mg/ml pepsin (Boehringer-Mannheim) solution in 0.2M citrate buffer (pH 4.0) were added to 4.5 ml of 4.4 mg/ml purified 7B6 antibody solution in PBS, and the mixture was incubated at 37° C. for 18 hours. The resulting digest in the mixture was separated by Ultrogel ACA 44 (2.6×84 cm)(IBF biotechnics) equilibrated with 0.1M phosphate buffer (pH 7.0). Fractions containing F(ab)$_2$ were collected and concentrated with Centricon 30 (Amicon).

Then, an aliquot of the F(ab)$_2$ thus obtained was reduced as follows: 1/10 volumes of 0.1M phosphate buffer (pH 6.0) containing 0.1M 2-mercaptoethylamine and 5 mM of ethylenediamine tetraacetic acid (EDTA) were added to 1.2 ml of 0.1M phosphate buffer (pH 7.0) containing 3.3 mg of F(ab)$_2$, and the mixture was allowed to react at 37° C. for 30 minutes. The mixture containing the reduced substances was separated by Superose 12 (1.5×50 cm) (Pharmacia) equilibrated with 0.1M phosphate buffer (pH 6.0) containing 5 mM EDTA to give fractions containing Fab. The fractions were concentrated with Centricon 10 (Amicon).

On the other hand, 23.6 mg of ε-maleimidocaproyloxysuccinimide (EMCS, Dojinkagaku) dissolved in 250 μl of N,N-dimethylformamide was added to 17.2 mg of HRP (Sigma) dissolved in 2 ml of 0.1M phosphate buffer (pH 7.0), and the mixture was allowed to react at 30° C. for 15 minutes. The precipitate thus generated was removed by centrifugation, and the supernatant was passed through PD-10 (Pharmacia) equilibrated with 0.1M phosphate buffer (pH 6.0) to remove low molecular substances, whereby the maleimide derivative of HRP was obtained.

The obtained fraction containing the maleimide derivative of HRP and the concentrated Fab were mixed each other so that the molar ratio of HRP and Fab was 1:1 and allowed to react at 30° C. for 1 hour. Fab labelled with HRP was separated from unlabelled materials using Superose 12 (1.5× 50 cm) equilibrated with 0.1M phosphate buffer (pH 6.5). Thus, Fab fragment (0.62 mg) labelled with HRP was obtained.

EXAMPLE 7

Sandwich EIA

Fifty μl of a standard solution of N-peptide(1–67) or a sample was placed in each of several test tubes. Then, 250 μl of Buffer C was added to each test tube. Each one of beads coated by the KY-ANP-III antibody produced in Example 3 was added to each test tube. Each test tube was horizontally shaken at 200 strokes per minute at 25° C. for 2 hours (first reaction), the solution in each test tube was removed by aspiration, and the test tubes were washed three times with 2 ml of Buffer D. Then, the second reaction was conducted as follows. Three hundred μl of HRP-labelled 7B6 antibody solution diluted with Buffer D containing 0.1% BSA was added to each test tube (200 ng/test tube), and the test tubes were horizontally shaken at 200 strokes per minute at 25° C. for 2 hours. The solution in the test tubes was removed by aspiration, and the test tubes were washed five times with 2 ml of Buffer D. Then, as a substrate solution, 300 μl of 0.01M citrate buffer (pH 5.0) containing 8.5 mg/ml of 2,2'-azino-bis(3-ethylbenzothiazoline-6-sulfonic acid) (ABTS, Boehringer-Mannheim) and 2 mM of $H_2O_2$ were added to each test tube, the test tubes were allowed to stand at 25° C. for precisely 30 minutes, and then, 2 ml each of stop solution was added to the test tubes. The absorbance at 415 nm of each of the mixtures was measured by a spectrophotometer (UV-264, Shimadzu Corporation). Distilled water was used as a blank.

Figure 4:
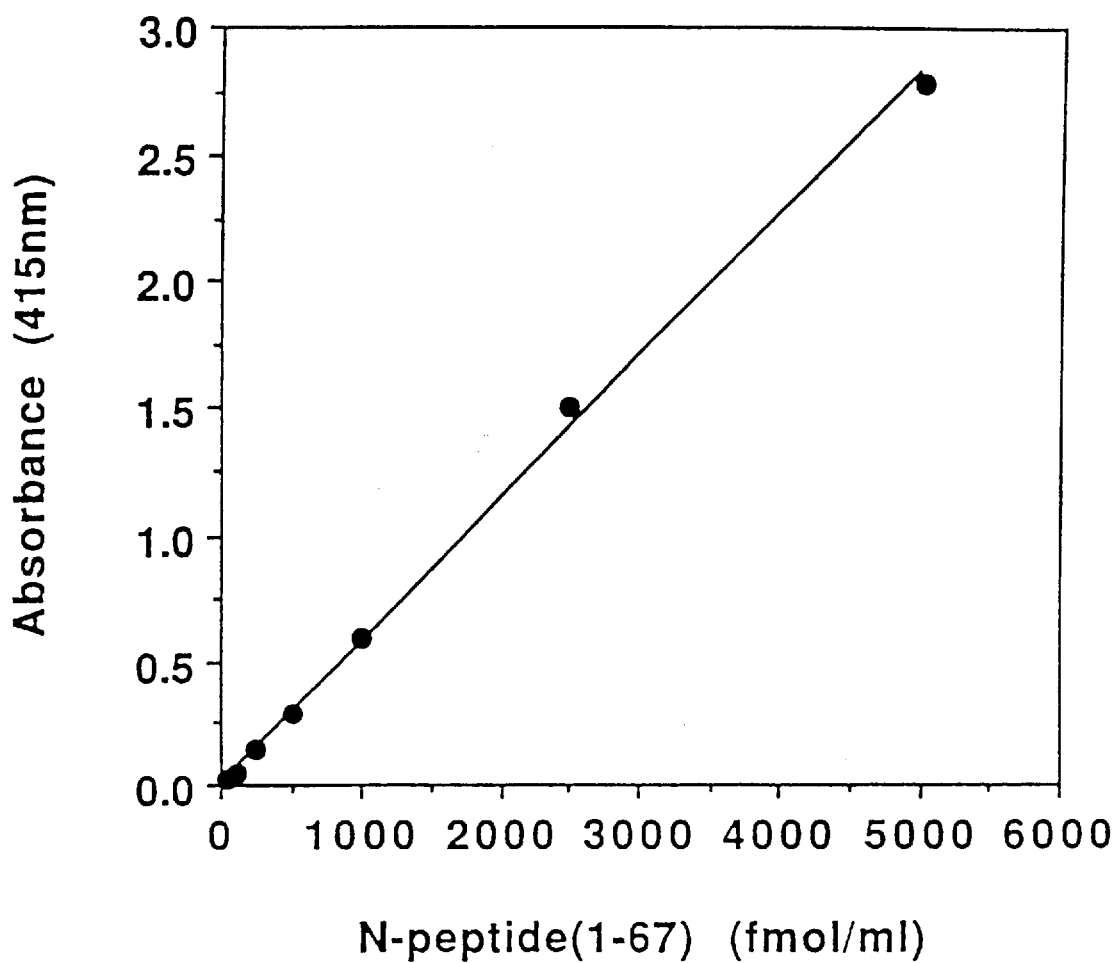
FIG. 4 shows a standard curve in the sandwich EIA in the present invention.

A standard curve obtained from the above-mentioned sandwich EIA is shown in FIG. 4. The enzyme activity retained on the bead was proportional to the concentration of N-peptide(1–67) in the range of 0 to 5000 fmol/ml. The lowest sensitivity detectable was 25 fmol/ml. A reproducibility test was conducted using 3 samples of human plasma, of which the results are shown in Tables 4 and 5. In the intra-assay reproducibility test, CV was 1.2% to 4.6%, and in the inter-assay reproducibility test, CV was 5.9% to 15.0%.

TABLE 4

Intra-assay reproducibility by Sandwich EIA

| Sample | n | Mean ± SD fmol/ml | CV % |
|---|---|---|---|
| Human plasma L | 5 | 204 ± 9.5 | 4.6 |
| Human plasma M | 5 | 730 ± 8.9 | 1.2 |
| Human plasma H | 5 | 2447 ± 65.6 | 2.7 |

TABLE 5

Inter-assay reproducibility by Sandwich EIA [a]

| Sample | n | Mean ± SD fmol/ml | CV % |
|---|---|---|---|
| Human plasma L | 4 | 222 ± 33.3 | 15.0 |
| Human plasma M | 4 | 787 ± 66.1 | 8.4 |
| Human plasma H | 4 | 2511 ± 148.3 | 5.9 |

[a] Four separate assays were performed in duplicate over 4 days.

Figure 5:
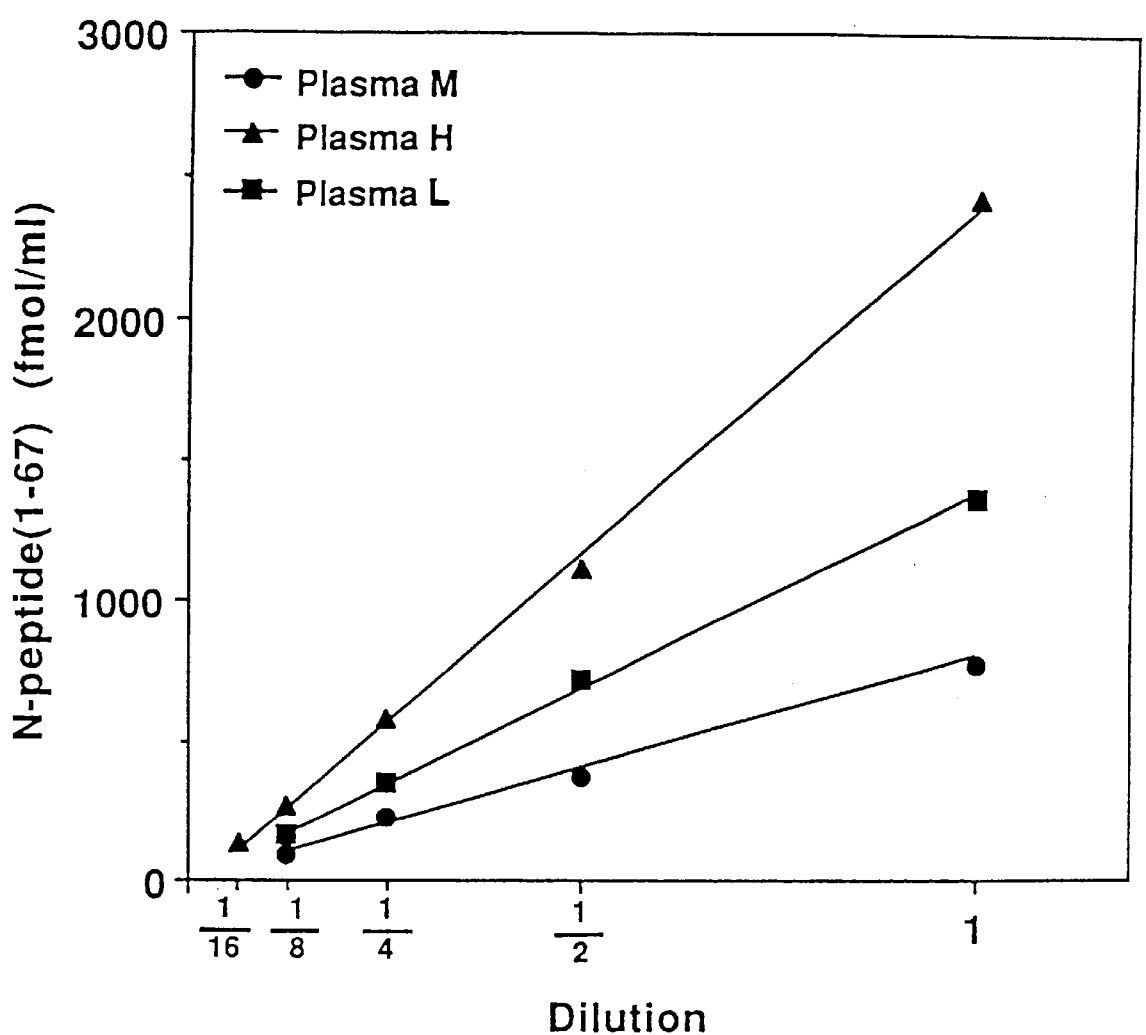
FIG. 5 shows a dilution curve tested in clinical samples by the sandwich EIA of the present invention.

Next, a dilution test was conducted using human plasmas. Serial two-fold dilutions with Buffer C were performed as three samples of human plasma. The samples thus obtained were measured by the sandwich EIA in the same way as described in Example 7. The results are shown in FIG. 5. The data indicates that in any concentration each point is on a straight line which approximately intersects at the zero point.

Thus, in the same way as in Example 5, it was confirmed that N-peptide can be determined by the sandwich EIA of the present invention with good precision without being influenced by the other components in the plasma.

Furthermore, a recovery test for added substance was conducted using human plasma. Three samples of human plasma were diluted by a factor of two with a standard N-peptide(1–67) solution containing N-peptide in a series of concentrations. The samples thus obtained were measured by the sandwich EIA in the same way as described above. The results are shown in Table 6. The recovery of the added N-peptide was 82% to 103%. Thus, it was confirmed that various N-peptides in human plasma and the standard N-peptide show a similar reactivity in the sandwich EIA of the present invention.

TABLE 6

Recovery test for added substance by sandwich EIA

| Sample | Endogenous N-peptide (fmol/ml) | Added (fmol/ml) | Found [a] (fmol/ml) | Recovery (%) |
|---|---|---|---|---|
| Human plasma L | 116 | 50 | 50 | 100 |
| | 116 | 125 | 103 | 82 |
| | 116 | 250 | 224 | 90 |
| Human plasma M | 382 | 250 | 240 | 96 |
| | 382 | 500 | 480 | 96 |
| | 382 | 1250 | 1232 | 99 |
| Human plasma H | 1234 | 500 | 504 | 101 |
| | 1234 | 1250 | 1286 | 103 |
| | 1234 | 2500 | 2526 | 101 |

[a] Increase over endogenous N-peptide

The correlation between the values (X) obtained from 14 samples of human plasma which were measured by the sandwich and the corresponding values (Y) measured by the sandwich EIA was examined. As a result, a correlation equation was represented by Y=0.79X−132(fmol/ml) and a correlation coefficient R was 0.99.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A monoclonal antibody that specifically binds an epitope of human atrial natriuretic polypeptide (γhANP 1–98) from the 43 position to the 67 position.

2. The monoclonal antibody according to claim 1, wherein the monoclonal antibody is 7B6.

3. An immunoassay kit of N-peptide or a precursor thereof comprising the monoclonal antibody of claim 1 or 2.

* * * * *